US010428201B2

(12) United States Patent
Ghosh-Dastidar et al.

(10) Patent No.: US 10,428,201 B2
(45) Date of Patent: Oct. 1, 2019

(54) PLASTICIZER COMPOSITIONS AND METHODS FOR MAKING PLASTICIZER COMPOSITIONS

(71) Applicant: Dow Global Technologies LLC, Midland, MI (US)

(72) Inventors: Abhijit Ghosh-Dastidar, East Brunswick, NJ (US); Manish Mundra, Collegeville, PA (US)

(73) Assignee: Dow Global Technologies LLC, Midland, MI (US)

( * ) Notice: Subject to any disclaimer, the term of this patent is extended or adjusted under 35 U.S.C. 154(b) by 40 days.

(21) Appl. No.: 15/509,716

(22) PCT Filed: Oct. 14, 2015

(86) PCT No.: PCT/US2015/055482
§ 371 (c)(1),
(2) Date: Mar. 8, 2017

(87) PCT Pub. No.: WO2016/069266
PCT Pub. Date: May 6, 2016

(65) Prior Publication Data
US 2017/0247528 A1    Aug. 31, 2017

Related U.S. Application Data

(60) Provisional application No. 62/068,864, filed on Oct. 27, 2014.

(51) Int. Cl.
| | |
|---|---|
| *C08K 5/1515* | (2006.01) |
| *C07D 303/42* | (2006.01) |
| *C08G 59/02* | (2006.01) |
| *C11C 3/00* | (2006.01) |
| *C08G 65/32* | (2006.01) |
| *C07D 303/44* | (2006.01) |
| *C07D 301/12* | (2006.01) |

(52) U.S. Cl.
CPC .......... *C08K 5/1515* (2013.01); *C07D 301/12* (2013.01); *C07D 303/42* (2013.01); *C07D 303/44* (2013.01); *C08G 59/027* (2013.01); *C08G 65/32* (2013.01); *C11C 3/003* (2013.01)

(58) Field of Classification Search
CPC .. C08K 5/1515; C07D 301/12; C07D 303/42; C07D 303/44; C11C 3/003; C11C 3/008
See application file for complete search history.

(56) References Cited

U.S. PATENT DOCUMENTS

| | | | |
|---|---|---|---|
| 3,377,304 A | 4/1968 | Kuester et al. | |
| 2009/0287007 A1* | 11/2009 | Abraham | C07D 303/42 549/524 |
| 2013/0203907 A1* | 8/2013 | Kazemizadeh | C08K 5/0016 524/114 |
| 2013/0261322 A1* | 10/2013 | Darbha | B01J 21/04 549/523 |
| 2014/0113999 A1 | 4/2014 | Howard et al. | |

FOREIGN PATENT DOCUMENTS

| | | | |
|---|---|---|---|
| WO | 2011090812 A2 | 7/2011 | |
| WO | 2013119402 A1 † | 8/2013 | |
| WO | WO-2013119402 A1 * | 8/2013 | ........... C08K 5/0016 |
| WO | 2014072986 A1 | 5/2014 | |
| WO | 2014072987 A1 † | 5/2014 | |
| WO | 2014149723 A1 | 9/2014 | |

OTHER PUBLICATIONS

F. Galli, et al., Epoxy Methyl Soyate as Bio-Plasticizer: Two Different Preparation Strategies, 2014, pp. 601-606, vol. 37.
PCT/US2015/055182, International Search Report dated May 6, 2016.
PCT/US2015/055182, International Preliminary Report on Patentability dated May 2, 2017.
PCT/US2015/055182, Written Opinion of the International Searching Authority dated May 6, 2016.
European Application No. 15805333.0 Third Party Submission dated Jan. 16, 2018.
Japanese Application No. 2017-521117 Third Party Submission dated Jan. 19, 2018.

\* cited by examiner
† cited by third party

*Primary Examiner* — Robert C Boyle
(74) *Attorney, Agent, or Firm* — Husch Blackwell LLP

(57) ABSTRACT

The present disclosure is directed to a plasticizer composition, polymeric compositions containing the plasticizer composition, and coated conductors comprising the polymeric composition. The plasticizer composition comprises an epoxidized fatty acid alkyl ester having an APHA color value of less than 100, a triepoxide content of at least 6.5 weight percent, and an oxirane oxygen content of at least 5 grams oxirane per 100 grams of epoxidized fatty acid alkyl ester.

6 Claims, No Drawings

PLASTICIZER COMPOSITIONS AND METHODS FOR MAKING PLASTICIZER COMPOSITIONS

REFERENCE TO RELATED APPLICATIONS

The present application claims the benefit of U.S. Provisional Application No. 62/068,864, filed on Oct. 27, 2014.

FIELD

Various embodiments of the present invention relate to plasticizers derived from natural oils (e.g., oils derived from biological sources). Other aspects of the invention concern processes for producing such plasticizers.

INTRODUCTION

Plasticizers are compounds or mixtures of compounds that are added to polymer resins to impart softness and flexibility. Phthalic acid diesters (also known as "phthalates") are known plasticizers in many flexible polymer products, such as polymer products formed from polyvinyl chloride ("PVC") and other vinyl polymers. Examples of common phthalate plasticizers include di-isononyl phthalate, diallyl phthalate, di-2-ethylhexyl-phthalate, dioctyl phthalate, and diisodecyl phthalate. Other common plasticizers, used for high temperature applications, are trimellitates and adipic polyesters. Mixtures of plasticizers are often used to obtain optimum properties.

Phthalate plasticizers have recently come under intense scrutiny by public interest groups that are concerned about the negative environmental impact of phthalates and potential adverse health effects in humans (especially children) exposed to phthalates.

Epoxidized methyl ester of soybean oil (e.g., epoxidized fatty acid methyl ester, or "eFAME") can be used as a plasticizer for polyvinyl chloride ("PVC") and other polymers (natural rubber, acrylate, etc.) or alternately, it can be used as a primary or secondary plasticizer in a plasticizer blend (such as with epoxidized soybean oil ("ESO")). However, eFAME often contains various impurities that may cause color in plasticized compositions. Accordingly, improvements in such plasticizers are desired.

SUMMARY

One embodiment is a plasticizer composition, comprising:
  an epoxidized fatty acid alkyl ester,
  wherein said epoxidized fatty acid alkyl ester has an APHA color value of less than 100,
  wherein said epoxidized fatty acid alkyl ester has a triepoxide content of at least 6.5 weight percent based on the entire weight of said epoxidized fatty acid alkyl ester,
  wherein said epoxidized fatty acid alkyl ester has an oxirane oxygen content of at least 5 grams oxirane per 100 grams of epoxidized fatty acid alkyl ester.

Another embodiment is a process for producing a plasticizer composition, said process comprising:
  (a) providing a distilled fatty acid alkyl ester; and
  (b) subjecting said distilled fatty acid alkyl ester to an epoxidation process to thereby produce an epoxidized fatty acid alkyl ester,
  wherein said epoxidized fatty acid alkyl ester has a color value of less than 100 APHA,
  wherein said epoxidized fatty acid alkyl ester has a triepoxide content of at least 6.5 weight percent based on the entire weight of said epoxidized fatty acid alkyl ester,
  wherein said epoxidized fatty acid alkyl ester has an oxirane oxygen content of at least 5 grams oxirane per 100 grams of epoxidized fatty acid alkyl ester.

DETAILED DESCRIPTION

Various embodiments of the present invention concern plasticizers derived from natural oils. The plasticizers include a natural oil that has been epoxidized and esterified forming an epoxidized fatty acid alkyl ester ("eFAAE"). In preparing such plasticizers, the fatty acid alkyl ester used to prepare the eFAAE can first be distilled, then epoxidized. Such plasticizers can be employed with a variety of polymeric resins and in the making of various articles of manufacture.

Plasticizer

The present disclosure provides plasticizer compositions comprising an epoxidized fatty acid alkyl ester. A plasticizer is a substance that can lower the modulus and tensile strength, and increase flexibility, elongation, impact strength, and tear strength of a polymeric resin (typically a thermoplastic polymer) to which it is added. A plasticizer may also lower the melting point of the polymeric resin, which lowers the glass transition temperature and enhances processability of the polymeric resin to which it is added. In an embodiment, the present plasticizer is a phthalate-free plasticizer, or is otherwise devoid or substantially devoid of phthalate.

As noted above, the plasticizer includes an epoxidized fatty acid alkyl ester. Epoxidized fatty acid alkyl esters are typically prepared by subjecting a fatty acid alkyl ester to an epoxidation process. "Epoxidation" means a process of forming an epoxide, also known as an oxirane or alkylene oxide. As known in the art, fatty acid alkyl esters are alkyl esters of fatty acids. "Fatty acids" are carboxylic acids composed of an aliphatic chain typically containing 4 to 24 carbon atoms with a terminal carboxyl group (—COOH). The fatty acid can be saturated or unsaturated, and branched or unbranched, or mixtures thereof.

Preparation of fatty acid alkyl esters can be accomplished by any conventional or hereafter discovered techniques. In various embodiments, the fatty acid alkyl ester can be obtained using conventional techniques of transesterification of a natural oil with an alkyl alcohol (e.g., methyl alcohol). A "natural oil," as used herein, is an oil composed of fatty acid triglycerides and derived from a microbe (algae, bacteria), a plant/vegetable, and/or a seed. In an embodiment, natural oil includes genetically-modified natural oil. Natural oils do not include petroleum-derived oils. Non-limiting examples of suitable natural oils include beef tallow oil, canola oil, castor oil, corn oil, fish oil, linseed oil, palm oil, rapeseed oil, safflower oil, soybean oil, sunflower oil, tall oil, tung oil, and any combination thereof. In various embodiments, the fatty acid alkyl ester can be derived from a soybean oil. Alternatively, esterification of fatty acids (e.g., C18 fatty acids, such as oleic, linoleic, and linolenic acids) with alkyl alcohols can be used to prepare the fatty acid alkyl esters.

The alkyl alcohol employed in preparing the fatty acid alkyl ester can be selected based on the desired alkyl moiety of the fatty acid alkyl ester. For example, if a fatty acid methyl ester is desired, then a methyl alcohol (i.e., methanol) can be employed in the transesterification of the natural oil or esterification of the fatty acid. In various embodiments, the alkyl alcohol used to prepare the fatty acid alkyl ester can be selected from the group of methyl alcohol, ethyl alcohol, 1-propyl alcohol, 2-ethylhexyl alcohol, or mixtures of two or more thereof. Accordingly, the alkyl moiety of the fatty acid alkyl ester may be, for example, a methyl group, an ethyl group, a propyl group, a 2-ethylhexyl group, or mixtures of two or more thereof. In an embodiment, the fatty acid alkyl ester is a fatty acid methyl ester ("FAME").

Prior to epoxidation, the fatty acid alkyl ester is distilled. Any conventional or hereafter discovered distillation technique can be employed. In various embodiments, distillation can be performed with a wiped film evaporator ("WFE") and a condenser. In an embodiment, the distillation is performed employing a WFE at a temperature ranging from 120 to 360° C., from 140 to 200° C., or from 150 to 160° C. The condenser can have a temperature of 20° C. Additionally, WFE distillation may be performed at atmospheric pressure or under vacuum with pressures as low as a few millitorr.

In alternate embodiments, distillation can be performed in a conventional distillation column, under vacuum (e.g., 2 to 5 millimeters mercury), at a temperature of at least 200° C., at least 210° C., or at least 220° C. In such embodiments, the distillation temperature can be less than 360° C., less than 300° C., or less than 240° C. In a typical embodiment, distillation can be performed in a conventional distillation column at a temperature ranging from 200 to 240° C. and a pressure of 2 to 5 millimeters mercury.

The resulting distilled fatty acid alkyl ester can have an American Public Health Association ("APHA") color value of less than 100, less than 80, less than 60, less than 40, or less than 25. In various embodiments, the distilled fatty acid alkyl ester can have an APHA color value of at least 5, at least 10, or at least 15. APHA color values are determined according to the procedure described in the Test Methods section, below. Additionally, the distilled fatty acid alkyl ester can have an iodine number of at least 100, at least 110, at least 120, or at least 130. Generally, the distilled fatty acid alkyl ester can have an iodine number of less than 160, less than 150, less than 140, or less than 135. Iodine values are determined according to the procedure described in the Test Methods section, below.

Examples of suitable commercially available distilled fatty acid alkyl esters include, but are not limited to, SE 1885 fatty acid methyl ester, available from Felda-Iffco (Cincinnati, Ohio, USA), and SOYCLEAR™ 1500 fatty acid methyl ester, available from AG Processing, Inc. (Omaha, Nebr., USA).

Following distillation, the distilled fatty acid alkyl ester can be epoxidized to form an epoxidized fatty acid alkyl ester ("eFAAE"). During epoxidation of the fatty acid alkyl ester, an epoxide group can be formed at one or more unsaturation points in the fatty acid chain. An "epoxide group" is a three-member cyclic ether (also called oxirane or an alkylene oxide) in which an oxygen atom is joined to each of two carbon atoms that are already bonded to each other. Thus, "epoxidized fatty acid alkyl ester" and like terms mean a compound with at least one fatty acid alkyl ester moiety which contains at least one epoxide group.

Epoxidation of the fatty acid alkyl ester can be performed using any conventional or hereafter discovered epoxidation techniques. Epoxidation reactions are typically performed with percarboxylic acids or other peroxy compounds. By way of non-limiting example, an epoxidized fatty acid alkyl ester can be prepared by combining the fatty acid alkyl ester, hydrogen peroxide, and formic acid in 1:2:0.5 proportions, respectively. The ester and formic acid can first be combined and mixed together (e.g., stirred at a speed of 400 rpm) at 30° C. The hydrogen peroxide can then be added at an initial rate of 10 mL/hr. The rate of peroxide addition can then be slowly increased to the required flow rate depending on the exothermicity of the reaction. Addition is generally completed within an hour. The reaction temperature can then be raised to 40 or 50° C. and the reaction is continued until the oxirane oxygen value does not increase further. Thereafter, the stirring can be stopped, and layers can be separated. The oil layer can first be washed with water followed by dilute potassium hydroxide, and then again with water or brine. The oil layer can then be dried under vacuum.

It is known to those skilled in the art of using epoxidized vegetable oils or their derivatives as plasticizers that the presence of epoxy functionality enhances solubility in PVC. Increase in solubility in turn results in improved performance as a plasticizer. For this reason, monoepoxide, diepoxide, and triepoxide chains are desired components of the eFAME product. Triepoxides are the most desired, since they provide the highest epoxide (or oxirane oxygen) concentration on a unit-weight basis. On the other hand, methyl palmitates and methyl stearates are less desirable, since they are not very soluble in PVC. Therefore, increased amounts of these saturated components in the plasticizer can result in exudation (or spew) of the liquid from the polymer, rendering the finished article unusable over time. In addition, these saturated fractions also increase the freezing temperature (pour point) of the plasticizer, leading to added complexity in handling, storage, and transportation of the material.

In various embodiments, the resulting eFAAE (e.g., eFAME) can have a triepoxide content of at least 6.5 weight percent ("wt %"), at least 6.7 wt %, at least 7.0 wt %, at least 7.1 wt %, at least 7.2 wt %, at least 7.3 wt %, or at least 7.4 wt % based on the entire weight of the epoxidized fatty acid alkyl ester. As used herein, the term "triepoxide" denotes an epoxidized C18 fatty acid alkyl ester molecule having three epoxide groups on its alkyl tail. An example of a triepoxide is an alkyl linolenate (i.e., a C18 fatty acid alkyl ester) that has been epoxidized at each of the three unsaturation points on its alkyl tail. Triepoxide content is determined according to the procedure provided in the Test Methods section, below. Generally, the triepoxide content of the eFAAE can be less than 10 wt %, less than 9 wt %, or less than 8 wt % based on the entire weight of the eFAAE.

In various embodiments, the eFAAE (e.g., eFAME) can have a palmitate content of less than 12 wt %, less than 11.8 wt %, or less than 11.7 wt % based on the entire weight of the eFAAE. "Palmitates" are esters of palmitic acid, which is a saturated C16 fatty acid. Palmitate content is determined according to the procedure provided in the Test Methods section, below. Typically, the palmitate content of the eFAAE can be at least 10 wt %, at least 10.5 wt %, at least 11 wt %, or at least 11.5 wt % based on the entire weight of the eFAAE.

In various embodiments, the eFAAE (e.g., eFAME) can have a stearate content of less than 5 wt %, less than 4.8 wt %, or less than 4.6 wt % based on the entire weight of the eFAAE. "Stearates" are esters of stearic acid, which is a saturated C18 fatty acid. Stearate content is determined according to the procedure provided in the Test Methods section, below. Typically, the stearate content of the eFAAE can be at least 4 wt %, at least 4.2 wt %, or at least 4.4 wt % based on the entire weight of the eFAAE.

In various embodiments, the eFAAE (e.g., eFAME) can comprise fatty acid dimers in a concentration of at least 0.1 wt %, at least 0.2 wt %, at least 0.4 wt %, at least 0.8 wt %, or at least 1.2 wt % based on the entire weight of the eFAAE. Fatty acid dimer content can be determined by chromatographic analyses, as described in the Test Methods below. Fatty acid dimers include molecules having two combined fatty acid aliphatic chains. The fatty acid aliphatic chains can be saturated, unsaturated, and/or epoxidized. Non-limiting examples of fatty acid dimers include molecules having structures such as:

the eFAAE can have an APHA color value that is at least 10, at least 20, at least 30, at least 40, or at least 50 percent less than the APHA color value of the above-described distilled fatty acid alkyl ester. Additionally, the eFAAE can have an APHA color value that is up to 65 percent less than the APHA color value of the above-described distilled fatty acid alkyl ester.

In various embodiments, the eFAAE can have an oxirane oxygen content of at least 5, at least 5.2, at least 5.4, at least 5.6, at least 5.8, at least 6.0, or at least 6.2 grams oxirane per 100 grams of epoxidized fatty acid alkyl ester. Generally, the eFAAE can have an oxirane oxygen content of up to 7.0, or up to 6.6 grams oxirane per 100 grams of epoxidized fatty

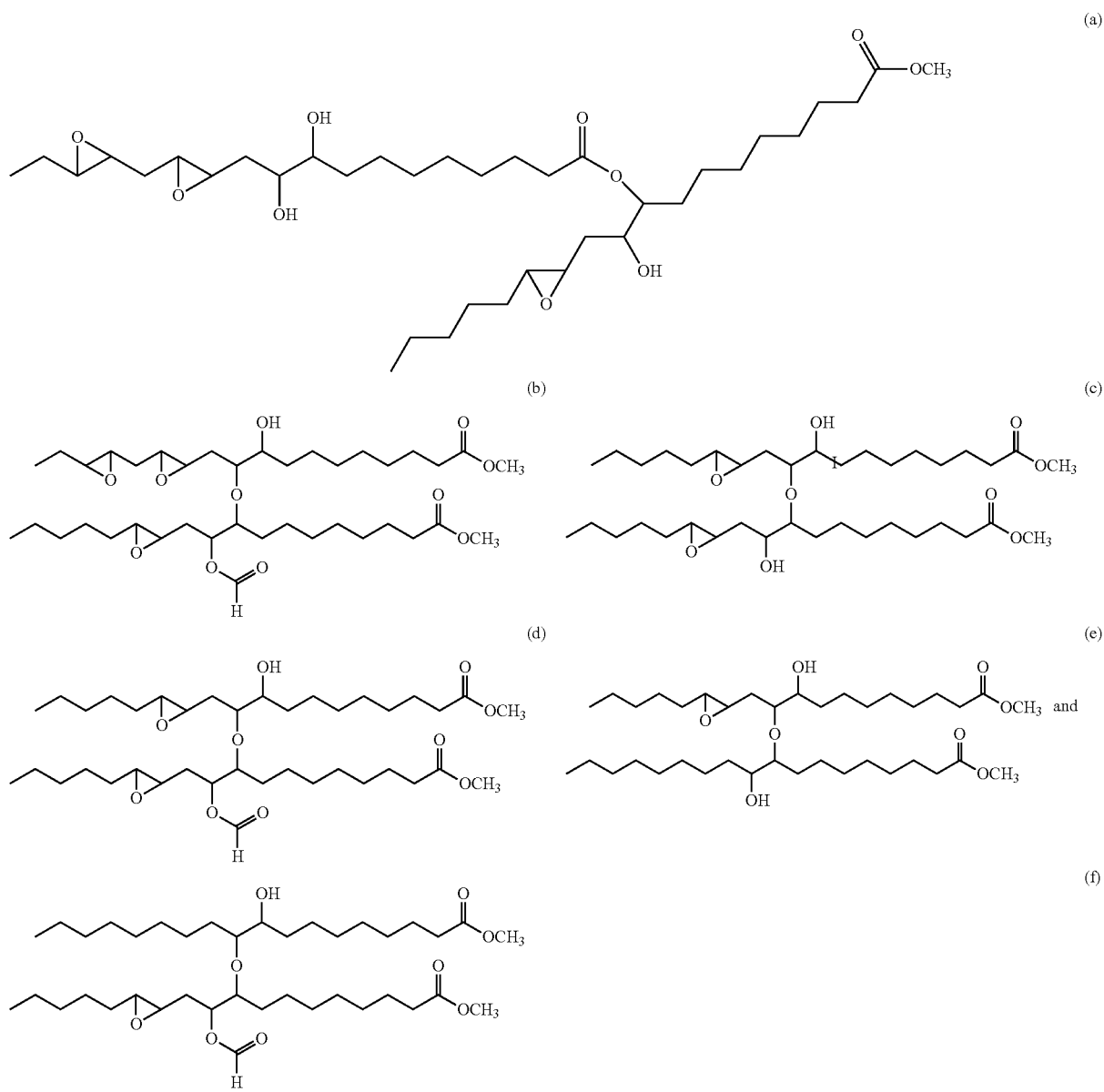

In various embodiments, the eFAAE (e.g., eFAME) can have an APHA color value of less than 100, less than 80, less than 60, less than 40, less than 20, or less than 15. Additionally, the eFAAE can have an APHA color value of at least 1, at least 2, or at least 5. In one or more embodiments, acid alkyl ester. Oxirane oxygen content is determined according to the procedure described in the Test Methods section, below.

In various embodiments, the eFAAE can have an iodine value of less than 9, less than 8, less than 7, less than 6, less than 5, less than 4, or less than 3 grams iodine per 100 grams of epoxidized fatty acid alkyl ester. Generally, the eFAAE can have an iodine value of at least 1, or at least 2 grams iodine per 100 grams of epoxidized fatty acid alkyl ester.

In one or more embodiments, the plasticizer composition can also include an epoxidized natural oil ("eNO"). As noted above, a "natural oil" is an oil composed of fatty acid triglycerides and derived from a microbe (algae, bacteria), a plant/vegetable, and/or a seed. The term "epoxidized natural oil," as used herein, is a natural oil wherein at least one fatty acid moiety contains at least one epoxide group. Epoxidation may occur by way of reaction of the natural oil with percarboxylic acid and/or other peroxy compounds, in a similar manner to the epoxidation methods described above for producing eFAAE.

Non-limiting examples of suitable eNOs include epoxidized algae oil, epoxidized beef tallow oil, epoxidized canola oil, epoxidized castor oil, epoxidized corn oil, epoxidized fish oil, epoxidized linseed oil, epoxidized palm oil, epoxidized rapeseed oil, epoxidized safflower oil, epoxidized soybean oil, epoxidized sunflower oil, epoxidized tall oil, epoxidized tung oil, and any combination thereof.

In an embodiment, the epoxidized natural oil comprises epoxidized soybean oil ("eSO").

When an epoxidized natural oil is present, the plasticizer composition can contain relative amounts of eNO (e.g., eSO) to eFAAE (e.g., eFAME) in a weight ratio in the range of from greater than (">") 0:less than ("<") 100 to <100:>0, more typically from 10:90 to 90:10, more typically from 20:80 to 80:20, and even more typically from 30:70 to 70:30. Weight ratios are based on total weight of the plasticizer composition.

Polymeric Composition

The present disclosure provides a polymeric composition. In an embodiment, a polymeric composition is provided which includes a polymer and the plasticizer composition as disclosed above.

Non-limiting examples of suitable polymers include polysulfides, polyurethanes, acrylics, epichlorohydrins, nitrile rubber, chlorosulfonated polyethylene, chlorinated polyethylene, polychloroprene, styrene butadiene rubber, natural rubber, synthetic rubber, EPDM rubber, propylene-based polymers, ethylene-based polymers, and vinyl chloride resins. The term "propylene-based polymer," as used herein, is a polymer that comprises a majority weight percent polymerized propylene monomer (based on the total amount of polymerizable monomers) and optionally may comprise at least one polymerized comonomer. The term "ethylene-based polymer," as used herein, is a polymer that comprises a majority weight percent polymerized ethylene monomer (based on the total weight of polymerizable monomers) and optionally may comprise at least one polymerized comonomer.

The term "vinyl chloride resin," as used herein, is a vinyl chloride polymer, such as polyvinyl chloride ("PVC"), or a vinyl chloride copolymer such as vinyl chloride/vinyl acetate copolymer, vinyl chloride/vinylidene chloride copolymer, vinyl chloride/ethylene copolymer or a copolymer prepared by grafting vinyl chloride onto ethylene/vinyl acetate copolymer. The vinyl chloride resin can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer or acrylonitrile-butadiene-styrene polymer.

In an embodiment, the polymer comprises a vinyl chloride resin.

In an embodiment, the polymer comprises PVC.

In an embodiment, when the polymeric composition includes polymer (e.g., PVC) in an amount of 100 parts per hundred resin ("phr"), eFAAE can be present in an amount ranging from 20 to 60 phr, eNO, when employed, can be present in an amount ranging from 20 to 60 phr, and filler can be present in an amount ranging from 0 to 35 wt % based on the entire weight of the polymeric composition.

Additives

The polymeric composition may include one or more of the following optional additives: a filler, a flame retardant, a heat stabilizer, an anti-drip agent, a colorant, a lubricant, a low molecular weight polyethylene, a hindered amine light stabilizer, a UV light absorber, a curing agent, a booster, a retardant, a processing aid, a coupling agent, an antistatic agent, a nucleating agent, a slip agent, a viscosity control agent, a tackifier, an anti-blocking agent, a surfactant, an extender oil, an acid scavenger, a metal deactivator, and any combination thereof.

In an embodiment, the polymeric composition includes PVC, the present plasticizer, a filler (calcium carbonate, clays, silica, and any combination thereof), metal soap stabilizers (zinc stearate or mixed metal stabilizers containing Ca, Zn, Mg, Sn, and any combination thereof), a phenolic or related antioxidant, and a processing aid.

Coated Conductor

The present disclosure provides a coated conductor. The coated conductor includes a conductor and a coating on the conductor, the coating being formed from the polymeric composition described above.

A "conductor," as used herein, is one or more wire(s) or fiber(s) for conducting heat, light, and/or electricity. The conductor may be a single-wire/fiber or a multi-wire/fiber and may be in strand form or in tubular form. "Wire" means a single strand of conductive metal, e.g., copper or aluminum, or a single strand of optical fiber. Non-limiting examples of suitable conductors include metals such as silver, gold, copper, carbon, and aluminum. The conductor may also be optical fiber made from either glass or plastic.

The coated conductor may be flexible, semi-rigid, or rigid. The coating (also referred to as a "jacket" or a "sheath" or "insulation") is on the conductor or on another polymeric layer around the conductor. A cable is one example of a coated conductor. "Cable" means at least one wire or optical fiber within a sheath (e.g., an insulation covering or a protective outer jacket). Typically, a cable is two or more wires or optical fibers bound together, typically in a common insulation covering and/or protective jacket. The individual wires or fibers inside the sheath may be bare, covered or insulated. Combination cables may contain both electrical wires and optical fibers. The cable can be designed for low, medium, and/or high voltage applications. Typical cable designs are illustrated in U.S. Pat. Nos. 5,246,783, 6,496,629 and 6,714,707.

Test Methods

Color Measurement

Measure liquid color according to ASTM standards D1209 and E313 using a BYK Gardner LCS III™ instrument and measure in APHA units. Set up the bench-top instrument and perform calibration check to insure the instrument is working within specifications. Measure sample color using the protocol listed below:

Set LCS III to measure Hazen/Alpha indices;
Measure each sample via syringe (10 mL) into individual calibrated cuvettes;
Place each loaded cuvette into the LCS III and press the test button; a Hazen/Alpha number is generated. Record this number, remove the sample and place back into the LCS III to measure a second time (record data). Repeat for a third time (record data).
Remove the loaded cuvette and set aside; reset the LCS III to measure Yellowness Index, measure the same cuvette for Yellowness Index (record three measurements).

Content Analysis of eFAME

The samples are analyzed using a gas chromatography ("GC") system with the following conditions:

| | |
|---|---|
| Instrument: | Agilent 6890 GC ™ |
| Column: | RTx-Biodiesel TG ™ (Restek), 15 m × 0.32 mm × 0.1-μm film |
| Injection: | Split, Restek precision double wool liner |
| Injection Volume: | 1.0 μL |
| Detection: | flame ionization (FID) |
| Carrier Gas: | He |
| Carrier Pressure: | 8 psi, constant pressure |
| Split flow: | 123 mL/min |
| Split ratio: | 40 |
| Hydrogen: | 30 mL/min |
| Air: | 350 mL/min |
| Makeup: | 25 mL/min |
| Injector Temp: | 340° C. |
| Detector Temp: | 350° C. |
| Temperature Program: | Initial Temp: 60° C. for 1 min. Ramp Rate: 15° C./min Final Temp: 350° C. for 20 min |
| Data System: | Thermo Atlas v 8.2 |

Oxirane Oxygen Content

Measure oxirane oxygen content according to American Oil Chemist Society ("AOCS") Official Method Cd 9-57.

Iodine Value

Measure iodine value according to AOCS Official Method Cd 1-25.

Tensile Strength and Elongation

Measure tensile strength and elongation according to ASTM method D638.

Materials

The following materials are employed in the Examples, below.

SOYCLEAR™ 1500 is a distilled (>200° C.) fatty acid methyl ester having an APHA color value of 23 and an iodine number of 134 grams iodine per 100 grams of fatty acid methyl ester ("g $I_2$/100 g"). SOYCLEAR™ 1500 is commercially available from AG Processing, Inc., Omaha Nebr., USA.

SE 1885 is a distilled (200 to 230° C.) fatty acid methyl ester having an APHA color value of 21 and an iodine number of 132 g $I_2$/100 g. SE 1885 is commercially available from Felda Iffco, Cincinnati, Ohio, USA.

SOYGOLD™ 1100 is a non-distilled fatty acid methyl ester having an APHA color value of 239 and an iodine value of 133 g $I_2$/100 g. SOYGOLD™ 1100 is commercially available from AG Processing, Inc., Omaha Nebr., USA.

The epoxidized soybean oil is PLAS-CHEK™ 775, which has an APHA color value of 85 and an oxirane content of 7.0%, and is commercially available from Ferro Corporation, Mayfield Heights, Ohio, USA.

The polyvinyl chloride ("PVC") employed is OXYVINYLS™ 240F, commercially available from Occidental Chemical Corporation, Dallas, Tex., USA.

The calcium carbonate ($CaCO_3$) employed is HUBERCARB™ Q3, which is untreated and has a median particle size of 3.2 μm (SediGraph™ method), and is commercially available from J.M. Huber Corporation, Edison, N.J., USA.

Zinc stearate is commercially available from Sigma-Aldrich, St. Louis, Mo., USA.

IRGANOX™ 1076 is a sterically hindered phenolic antioxidant having the chemical name octadecyl-3-(3,5-di-tert-butyl-4-hydroxyphenyl)-propionate, which is commercially available from BASF SE, Ludwigshafen, Germany.

Formic acid is commercially available from Sigma-Aldrich, St. Louis, Mo., USA.

Hydrogen peroxide ("$H_2O_2$") is commercially available from Sigma-Aldrich, St. Louis, Mo., USA.

Oleic acid is commercially available from Sigma-Aldrich, St. Louis, Mo., USA.

Methanol is commercially available from Sigma-Aldrich, St. Louis, Mo., USA.

Sulfuric acid is commercially available from Sigma-Aldrich, St. Louis, Mo., USA.

EXAMPLES

Sample Preparation

Sample 1

Sample 1 ("S1") is prepared by epoxidizing SOYCLEAR™ 1500, a distilled FAME. Epoxidation of the distilled FAME is accomplished by the following procedure. Fifty grams of the fatty acid methyl ester and a corresponding amount (25 grams) of formic acid are weighed in a 3-necked round-bottomed flask equipped with a mechanical stirrer, condenser and a dropper for controlled addition of $H_2O_2$. The mixture of FAME and formic acid are stirred at a speed of 400 rpm at 30° C. 100 g of hydrogen peroxide (30 to 50 wt %, depending on desired speed of reaction) is added at a rate of 10 mL/hr, and then the addition rate is slowly increased to the required flow rate depending on the exothermicity of the reaction. Addition is generally completed within an hour. The reaction temperature is then raised to 40-50° C., and the reaction is continued until the oxirane oxygen value does not increase further. Stirring is stopped and layers are separated. The oil layer is first washed with water followed by dilute potassium hydroxide and again with water or brine. The oil layer is then dried under vacuum.

Sample 2

Sample 2 ("S2") is prepared by epoxidizing SE 1885, a distilled FAME. Epoxidation of the distilled FAME is accomplished using the procedure described above for Sample 1.

Sample 3

Sample 3 ("S3") is prepared by epoxidizing SE 1885, a distilled FAME. Epoxidation of the distilled FAME is accomplished using the procedure described above for Sample 1.

Comparative Sample 1

Comparative Sample 1 ("CS1") is prepared by epoxidizing SOYGOLD™ 1100, a non-distilled FAME. Epoxidation of the non-distilled FAME is accomplished using the procedure described above for Sample 1.

Comparative Sample 2

Comparative Sample 2 ("CS2") is prepared by epoxidizing a non-distilled FAME, followed by distillation of the resulting eFAME at five different temperatures (CS2a-CS2e). Epoxidation of the non-distilled FAME is accomplished using the procedure described above for Sample 1.

Distill the resulting eFAME using the following procedure. Employing a 2-inch molecular still, degas the sample under the following conditions:

TABLE 1

Degassing (Pass 1):

| | |
|---|---|
| Wiped Film Evaporator ("WFE") Temperature (° C.) | 120 |
| System Pressure (Torr) | 8.000 |
| Condenser Temp. (° C.) | 15 |
| Wiper Speed (rpm) | 400 |
| Distillate Recovered (g) | 0.0 |
| Residue Recovered (g) | 975.0 |
| Total Recovered (g) | 975.0 |
| Sampling Time (min.) | 140 |
| Feed Rate (g/hr.) | 418 |
| Distillate Recovered (wt %) | 0.0 |
| Residue Recovered (wt %) | 100.0 |

Use the residue stream from Pass 1 as feed for the distillation in Pass 2.

TABLE 2

Distillation (Pass 2):

| Sample: | CS2a | CS2b | CS2c | CS2d | CS2e |
|---|---|---|---|---|---|
| WFE Temperature (° C.) | 150 | 160 | 170 | 140 | 145 |
| System Pressure (Torr) | 0.035 | 0.035 | 0.035 | 0.035 | 0.035 |
| Condenser Temp. (° C.) | 20 | 20 | 20 | 20 | 20 |
| Wiper Speed, rpm | 400 | 400 | 400 | 400 | 400 |
| Distillate Recovered (g) | 105.0 | 138.0 | 111.0 | 80.0 | 101.0 |
| Residue Recovered (g) | 40.0 | 25.0 | 6.0 | 100.0 | 40.0 |
| Total Recovered (g) | 145.0 | 163.0 | 117.0 | 180.0 | 141.0 |
| Sampling Time (min.) | 20 | 25 | 20 | 28 | 26 |
| Feed Rate (g/hr.) | 435 | 391 | 351 | 386 | 325 |
| Distillate Recovered (wt %) | 72.4 | 84.7 | 94.9 | 44.4 | 71.6 |
| Residue Recovered (wt %) | 27.6 | 15.3 | 5.1 | 55.6 | 28.4 |

Comparative Sample 3

Comparative Sample 3 ("CS3") is prepared by esterifying an oleic acid, epoxidizing the resulting FAME, and distilling the resulting eFAME at five different temperatures (CS3a-CS3e). Oleic acid (60 g), methanol (33.92 g), and sulfuric acid (1 wt % of acid, 0.6 g) are weighed in a 2 necked round-bottomed flask equipped with condenser and temperature sensor. The reaction mixture is heated in an oil bath at 65° C. under nitrogen flow for 6 hours. In some reactions water may form during the reaction, which can be azeotropically removed using toluene. After the reaction, the mixture is washed with water and potassium carbonate to remove unreacted oleic acid, followed by wash with water or brine. Excess alcohol is removed using a rotary evaporator. The final product is dried under vacuum.

Epoxidation of the resulting FAME is accomplished using the procedure described above for Sample 1.

The resulting eFAME is distilled using the following procedure. Employing a 2-inch molecular still, degas the sample under the following conditions:

TABLE 3

Degassing (Pass 1):

| | |
|---|---|
| WFE Temperature (° C.) | 120 |
| System Pressure (Torr) | 8.000 |
| Condenser Temp. (° C.) | 15 |
| Wiper Speed (rpm) | 400 |
| Distillate Recovered (g) | 3.0 |
| Residue Recovered (g) | 980.0 |

TABLE 3-continued

Degassing (Pass 1):

| | |
|---|---|
| Total Recovered (g) | 983.0 |
| Sampling Time (min.) | 110 |
| Feed Rate (g/hr) | 536 |
| Distillate Recovered (wt %) | 0.3 |
| Residue Recovered (wt %) | 99.7 |

Use the residue stream from Pass 1 as feed for the distillation in Pass 2.

TABLE 4

Distillation (Pass 2):

| Sample: | CS3a | CS3b | CS3c | CS3d | CS3e |
|---|---|---|---|---|---|
| WFE Temperature (° C.) | 140 | 145 | 150 | 160 | 170 |
| System Pressure (Torr) | 0.063 | 0.065 | 0.064 | 0.067 | 0.065 |
| Condenser Temp. (° C.) | 20 | 20 | 20 | 20 | 20 |
| Wiper Speed (rpm) | 400 | 400 | 400 | 400 | 400 |
| Distillate Recovered (g) | 143.0 | 154.0 | 122.0 | 145.0 | 148.0 |
| Residue Recovered (g) | 37.0 | 33.0 | 13.0 | 10.0 | 7.0 |
| Total Recovered (g) | 180.0 | 187.0 | 135.0 | 155.0 | 155.0 |
| Sampling Time (min.) | 22 | 22 | 17 | 19 | 20 |
| Feed Rate (g/hr.) | 491 | 510 | 476 | 489 | 465 |
| Distillate Recovered (wt %) | 79.4 | 82.4 | 90.4 | 93.5 | 95.5 |
| Residue Recovered (wt %) | 20.6 | 17.6 | 9.6 | 6.5 | 4.5 |

Example 1—Properties of S1-S3 and CS1

Using the test methods described above, measure the oxirane number, iodine value, and APHA color value of Samples S1-S3 and CS1. Results are provided in Table 5, below.

TABLE 5

Properties of S1-S3 and CS1

| Sample | Pre-Epoxidation Color (APHA) | Post-Epoxidation Color (APHA) | Color Reduction (%) | Oxirane Content (g/100 g) | Iodine Value (g/100 g) |
|---|---|---|---|---|---|
| S1 | 23 | 8 | 65 | 6.4 | 4.5 |
| S2 | 21 | 11 | 48 | 6.6 | 2.1 |
| S3 | 21 | 3 | 86 | 6.4 | 1.5 |
| CS1 | 239 | 81 | 66 | 6.5 | 2.7 |

The results provided in Table 5 indicate that all of Samples S1-S3 can function well as plasticizers for PVC, given their relatively high oxirane values and relatively low iodine values. Surprisingly, distillation prior to epoxidation results in very low color eFAME, similar, as shown with CS2 and CS3 below, to results achieved employing distillation after epoxidation. This is surprising because one skilled in the art would expect the epoxidation process to produce a number of color bodies in the resulting eFAME.

Example 2—APHA Color of CS2 and CS3

Analyze Comparative Samples CS2 and CS3 for APHA color values according to the test methods provided above. Results are provided in Table 6, below.

TABLE 6

APHA Color of CS2 and CS3

| Sample | WFE Temperature (° C.) | Average Color (APHA) | Std. Dev. |
|---|---|---|---|
| CS2* | — | 8 | 1 |
| CS2a | 140 | 3 | 1 |
| CS2b | 145 | 3 | 2 |
| CS2c | 150 | 4 | 1 |
| CS2d | 160 | 4 | 1 |
| CS2e | 170 | 6 | 2 |
| CS3* | — | 249 | 1 |
| CS3a | 140 | 18 | 0 |
| CS3b | 145 | 19 | 1 |
| CS3c | 150 | 22 | 2 |
| CS3d | 160 | 31 | 2 |
| CS3e | 170 | 41 | 1 |

*Prior to distillation

Comparing the results provided in Table 6 to those from Table 5, above, it can surprisingly be seen that similar color values can be achieved by employing distillation prior to epoxidation (S1-S3) compared to performing distillation after epoxidation (CS2 and CS3).

Example 3—Compositional Comparison

Analyze S1 (distillation before epoxidation) and CS2 (epoxidation before distillation) for palmitate content, stearate content, monoepoxide content, diepoxide content, triepoxide content, and dimer content according to the test methods provided above. The results are provided in Table 7, below. A typical soybean oil composition is provided for reference.

TABLE 7

Composition of S1 and CS2

| Sample | Palmitate (wt %) | Stearate (wt %) | Mono-epoxide (wt %) | Di-epoxide (wt %) | Tri-epoxide (wt %) | Dimers (wt %) | Total |
|---|---|---|---|---|---|---|---|
| CS2a | 25.19 | 9.46 | 34.37 | 31.84 | 1.35 | ND* | 102.21 |
| CS2b | 15.63 | 5.98 | 29.34 | 44.59 | 2.55 | ND | 98.09 |
| CS2c | 15.10 | 5.83 | 29.25 | 45.50 | 2.84 | ND | 98.52 |
| CS2d | 12.19 | 4.73 | 24.55 | 49.71 | 4.91 | ND | 96.09 |
| CS2e | 11.45 | 4.44 | 23.16 | 49.06 | 6.45 | ND | 94.56 |
| S1 | 11.60 | 4.50 | 25.00 | 47.50 | 7.00 | 1.40 | 97.00 |
| Soybean Oil | 10.60 | 4.00 | 23.30 | 53.70 | 7.60 | N/A | 99.20 |

*ND = not detected

From the data provided in Table 7, we see enrichment of saturates for 4 out of 5 Comparative Samples (CS2a-CS2d), and loss of triepoxy chains in all of them, although to a different extent, relative to Sample S1. The higher distillation temperature for the Comparative Samples decreases saturates and increases triepoxy chains, but that comes with somewhat increase in color, as seen in Table 6, above.

Example 4—Evaluation in PVC

For evaluation as a plasticizer in PVC, S2 is blended with expoxidized soybean oil in equal weight ratio. A PVC dry-blend is prepared in a Brabender mixing bowl with the eFAME/eSO blend. The composition of the PVC dry-blend is as follows: 100 parts per hundred resin ("phr") PVC; 68 phr calcium carbonate; 55 phr plasticizer (i.e., 50:50 eFAME/eSO); 3 phr zinc stearate; and 0.1 phr IRGANOX™ 1076. The dry-blend is prepared using the following steps:

(a) Make a "solids mixture" by mixing everything (except plasticizer and filler) in a container using a spatula;
(b) For mixing steps (c) through (e), use a 250-cm³ Brabender mixing bowl with sigma blades at 90° C. and 40 rpm;
(c) After two minutes warm-up, add the solids mixture and mix for 30 seconds;
(d) Add the plasticizer and mix for 6 minutes;
(e) Add the filler and mix for 60 seconds;
(f) Stop and remove the dry-blend.

By visual inspection, the plasticizer is easily absorbed by the PVC granules resulting in a dry powder, indicating very good compatibility of the plasticizer with PVC. The dry blend is then melt-mixed in the Brabender at 180° C. for two minutes with cam rotors at 40 rpm.

30-mil plaques are made from the compounded mixture by pressing at 180° C. for 5 minutes. Dogbone-shaped specimens are made for tensile and aged-tensile tests (100° C., 10 days). Small disks with 1.25-inch diameter are also prepared for weight loss and spew tests under two different aging conditions of 60° C. at 100% relative humidity for 14 days and 100° C. for 14 days in uncontrolled humidity.

The tensile stress and elongation for the unaged and aged PVC dogbones are shown as follows:
  Unaged Tensile stress (psi): 2,244
  Unaged elongation: 326%
  Aged Tensile stress (psi): 2,485
  Aged elongation: 257%

The retained tensile stress and elongation values show that the plasticizer made from the eFAME sourced from distilled FAME has good permanence property at higher temperature.

For aging in an oven under 60° C./100% RH, the PVC sample made with the plasticizer shows less than 2% weight loss over 2 weeks. In addition, no visible spew is present after 2 weeks. Similarly, aging at 100° C./14 days shows about 8.5% weight loss. Generally, if a compound does not lose more than 10% of its initial weight under such aging conditions, it indicates good permanence property for the plasticizer.

The invention claimed is:

1. A plasticizer composition, comprising:
   an epoxidized fatty acid alkyl ester, wherein said epoxidized fatty acid alkyl ester has
   (i) an APHA color value from at least 1 to less than 15;
   (ii) a triepoxide content from at least 6.5 weight percent to less than 8 weight percent, based on the entire weight of said epoxidized fatty acid alkyl ester, wherein the triepoxide is an epoxidized C18 fatty acid alkyl ester molecule having three epoxide groups on its alkyl tail;
   (iii) an oxirane oxygen content of at least 5 grams oxirane per 100 grams of epoxidized fatty acid alkyl ester;
   (iv) a fatty acid dimer content greater than 0.8 weight percent based on the entire weight of said epoxidized fatty acid alkyl ester; and
   (v) an iodine value from at least 1 gram to less than 5 grams per 100 grams of epoxidized fatty acid alkyl ester.

2. The plasticizer composition of claim 1, wherein said epoxidized fatty acid alkyl ester has a palmitate content from at least 10 wt % to less than 12 weight percent based on the entire weight of said epoxidized fatty acid alkyl ester; wherein said epoxidized fatty acid alkyl ester has a stearate content from at least 4 wt % to less than 5 weight percent based on the entire weight of said epoxidized fatty acid alkyl ester.

3. The plasticizer composition claim 1, further comprising an epoxidized natural oil.

4. The plasticizer composition of claim 1, wherein said epoxidized fatty acid alkyl ester has a fatty acid dimer content of at least 1.2 weight percent based on the entire weight of said epoxidized fatty acid alkyl ester; wherein said epoxidized fatty acid alkyl ester has a triepoxide content of from at least 6.5 weight percent to at least 7.0 weight percent based on the entire weight of said epoxidized fatty acid alkyl ester.

5. The plasticizer composition of claim 1, wherein said epoxidized fatty acid alkyl ester further comprises fatty acid dimers in a concentration of at least 1.2 weight percent, based on the entire weight of said epoxidized fatty acid alkyl ester.

6. The plasticizer composition of claim 1, wherein the epoxidized fatty acid alkyl ester has an oxirane oxygen content from at least 6.2 grams to up to 7.0 grams oxirane per 100 grams of epoxidized fatty acid alkyl ester.

* * * * *